United States Patent
Koike et al.

[11] Patent Number: 6,106,532
[45] Date of Patent: Aug. 22, 2000

[54] DEVICE FOR RETRIEVAL OF DEFECT CLOSURE DEVICES

[75] Inventors: Kazuyuki Koike, deceased, late of Suginami-ku, by Noriko Koike, Kanako Koike and Yusuke Koike, legal representatives; Toshiki Kobayashi, Kawagoe; Katsuya Miyagawa, Osaka; Yoshikazu Kishigami, Osaka; Toshihiro Kikuchi, Osaka, all of Japan

[73] Assignee: Nissho Corporation, Osaka-fu, Japan

[21] Appl. No.: 09/286,436

[22] Filed: Apr. 6, 1999

[30] Foreign Application Priority Data

Apr. 6, 1998 [JP] Japan .................................. 10-093171

[51] Int. Cl.[7] .................................................. A61B 17/10
[52] U.S. Cl. ............................................ 606/138; 606/213
[58] Field of Search .................................. 606/213, 138, 606/144, 139, 148, 151, 145

[56] References Cited

U.S. PATENT DOCUMENTS

| 5,337,736 | 8/1994 | Reddy . | |
| 5,474,565 | 12/1995 | Trott . | |
| 5,578,045 | 11/1996 | Das | 606/151 |
| 5,618,290 | 4/1997 | Toy et al. . | |
| 5,716,367 | 2/1998 | Koike et al. | 606/144 |
| 5,741,274 | 4/1998 | Lenker et al. | 606/142 |
| 5,766,157 | 6/1998 | Tilton, Jr. | 604/264 |
| 5,766,184 | 6/1998 | Matsuno et al. | 606/142 |
| 5,855,586 | 1/1999 | Habara et al. | 606/144 |
| 5,904,703 | 5/1999 | Gilson | 606/213 |

FOREIGN PATENT DOCUMENTS

| 0556564 | 8/1993 | European Pat. Off. . |
| 2616666 | 12/1988 | France . |
| 9406357 | 3/1994 | WIPO . |
| 9717021 | 5/1997 | WIPO . |

*Primary Examiner*—Michael Buiz
*Assistant Examiner*—Kevin Truong
*Attorney, Agent, or Firm*—Birch, Stewart, Kolasch & Birch, LLP

[57] ABSTRACT

A device for retrieval of defect closure devices, comprising a closure-catch catheter having at a distal end thereof a closure-catching device and at a proximal end thereof, a grip for operating the closure-catching. An elongated sheath having a lumen and is provided at the proximal end thereof with a lateral injection tube and hemostatic device. The catheter is moveably insertable in the lumen.

6 Claims, 6 Drawing Sheets

DEVICE FOR RETRIEVAL OF DEFECT CLOSURE DEVICES

BACKGROUND OF THE INVENTION

The present invention relates to a device for retrieval of defect closure devices and, more particularly, to a device for retrieving a closure device from a repaired site in the body of a patient in cases where the recovery of a condition of patient is not so well after repair operation of vascular defects or cardiac defects or where the closure device has fallen away or dislodged after operation.

At the present time, Fontan operations have been used for repair operations of complex cardiac anomalies such as single ventricle. In this operation, a single ventricle is used for the systemic circulation system, and for pulmonary circulation a vein of the systemic circulation system is directly connected to a pulmonary artery, whereby cardiac function is repaired. However, this operation frequently makes it difficult to perform postoperative management since a considerable decrease of cardiac output may occur because of increase of a pulmonary vascular resistance or transient ventricular hypofunction. The increase of pulmonary vascular resistance is caused by spasm of the pulmonary circulation system.

To avoid the increase of pulmonary vascular resistance and the considerable decrease of cardiac output, it is general practice for the above operation to form a small fenestration or perforation of about 4 mm between atria (most cases, the interatrial septum is made of an artificial membrane), thereby allowing the blood to flow through the small fenestration or perforation. This procedure followed by formation of the small fenestration or perforation is a Fontan fenestration. The closure treatment of the small fenestration after Fontan fenestration is mainly carried out by surgical operation. However, this surgical operation is followed by thoracotomy of a patient in addition to the treatment of the affected area. Thus, such surgical incision is a great burden to a patient. In particular, in case of a child patient, this burden is considerably large.

Recently, percutaneous transluminal therapeutic catheterization has been adopted as a noninvasive procedure to repair endocardial defects. For example, closure of atrial septal defects is carried out by transveneously inserting an intercardiac catheter into the heart and occluding the defect with an occluder. Further, the percutaneous transluminal therapeutic catheterization is applied to closure treatment of the small fenestration after Fontan fenestration with a closure device.

However, in case of the closure treatment of the small fenestration after Fontan fenestration with the closure device of the prior art, adhesion of thrombus may result from a large closure plate. Thus, there is a high risk of complications. Further, in cases where the closure device has fallen away or dislodged after operation, it is difficult to retrieve the closure device due to shape or size of the closure device.

SUMMARY OF THE INVENTION

It is an object of the present invention to provide a device for retrieval of defect closure devices, especially suitable for retrieval of an improved defect closure device for transcatheter operations, which has now been developed by the present inventors and is illustrated in FIG. 6. This improved defect closure device comprises an easily foldable closure member 31 with a shape-restoring force, an easily inflective fixing member 32 for fixing the closure member 31 to a tissue surrounding a defect aperture, and an easily inflective elastic member 33 for holding the closure member and the fixing member in close proximity to one another, the elastic member being respectively fixed at either end thereof to the fixing member and closure member. This closure device enables safe and reliable closure of fenestration and is simple in configuration, easy to operate, easy to retrieve and less in adhesion of thrombus.

According to the present invention, the above object is achieved by providing a device for retrieval of defect closure devices, which comprises a closure-catch catheter having at a distal end thereof a closure-catching means and at a proximal end thereof a grip for operating the closure-catching means, and an elongated sheath having a lumen and being provided at the proximal end thereof with a lateral injection tube and hemostatic means, said catheter being moveably insertable in the lumen.

The closure-catching means is preferably made into an arrowhead or a configuration which is not transformed when retrieving the closure device out of the patient's body after is caught of the closure device.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

Figure 1:
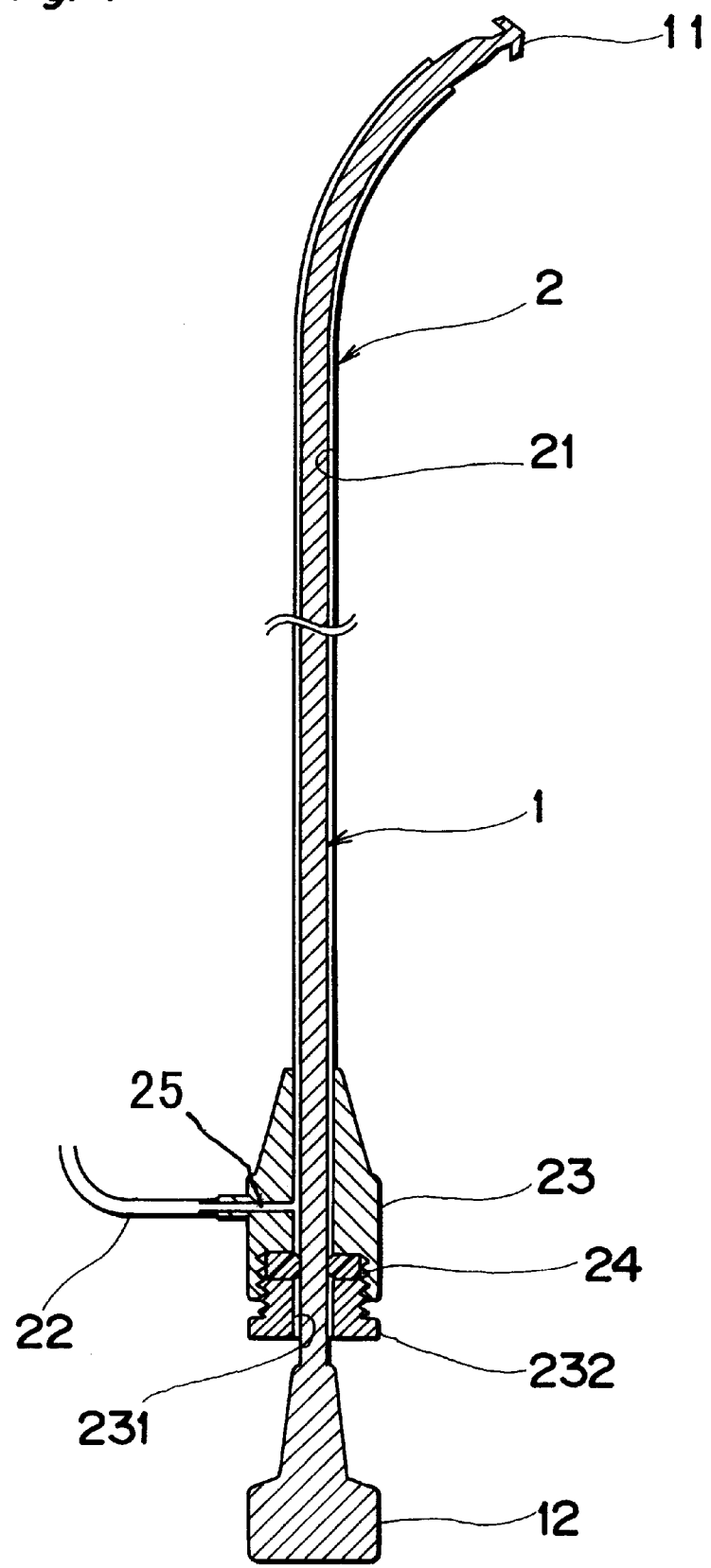
FIG. 1 is a vertical section view illustrating one embodiment of a device for retrieval of defect closure devices according to the present invention.

Referring now to FIG. 1, there is shown a device for retrieval of defect closure devices according to the present invention. The device comprises a closure-catch catheter 1 for catching a closure device and an elongated sheath 2 having a lumen 21 for holding the catheter 1 inserted therein. The closure-catch catheter 1 is provided at a distal end thereof with closure-catching means 11 for catching the closure device and at a proximal end thereof with a finger grip 12 for manipulating the catheter 1 with a finger. The elongated sheath 2 has a lumen 21 holding the closure-catch catheter 1 movably inserted therein and is provided at a proximal end thereof with a lateral injection tube 22 and hemostatic means such as packing 24 or O-ring.

Preferably, closure-catching means 11 is formed into an arrowhead or a like configuration which does not change in shape during retrieval of the closure device 3.

The closure-catch catheter 1 is an elongated solid member provided at a distal end thereof with means 11 for catching closure device and at a proximal end thereof with a finger grip 12 for manipulating the catheter 1 with a finger. As a material for closure-catch catheter 1, there may be used one or more materials selected from the group consisting of fluoroplastics such as polytetrafluoroethylene; synthetic resins such as polypropylene, polyethylene, polyester and the like; and meshed or coiled stainless steels such as SUS 304.

The sheath 2 is an elongated tubular member having a lumen 21 which enables the catheter 1 to be removably inserted thereinto and being provided at a proximal end thereof with a connector 23 having an insertion hole 231 for the catheter 1. The connector 23 is provided at its lateral with a side port 25 and at a proximal end with a threaded bore formed coaxially with the lumen of the connector 23. The side port 25 is communicated with the lumen 21 of the sheath 2 and connected with a lateral infusion tube 22 through which a heparinized physiological saline or the like solution is infused into the blood vessel through the sheath 2 to prevent blood coagulation during retrieve of the closure device.

The connector 23 is further provided with a hemostatic means or hemostatic valve to prevent the blood leakage during retrieve of the closure device. In this embodiment, the hemostatic means is composed of a packing 24 with a through-hole at the center thereof. The packing 24 is arranged in the threaded bore of the connector 23 and fixed within the lumen of the connector 23 by a screw bolt 232 with a through-hole at the center thereof to form a hermetic seal between the catheter 1 and connector 23.

As a material for the sheath, there may be used a material similar to those used for the closure-catch catheter 1. Preferred materials are mesh or coiled stainless steels such as SUS 304, which are not deformed by stress acting in the longitudinal direction of the sheath.

Explanation will be made on how to use the device for retrieval of defect closure devices according to the present invention, making reference to FIGS. 2–5.

Figure 2:
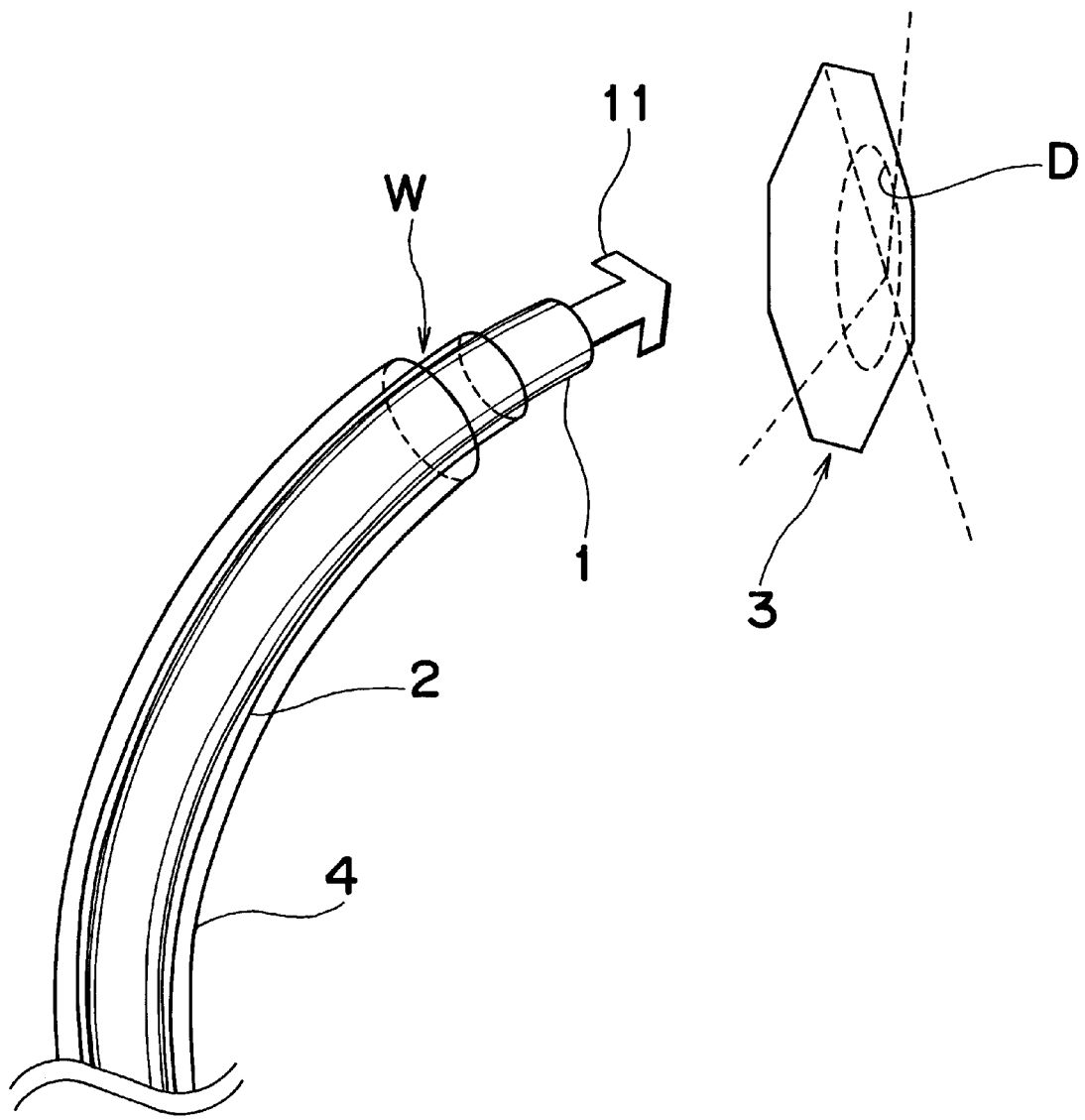
FIGS. 2 to 5 are views illustrating retrieving procedures with the device for retrieve of closure devices according to the present invention.
Figure 3:
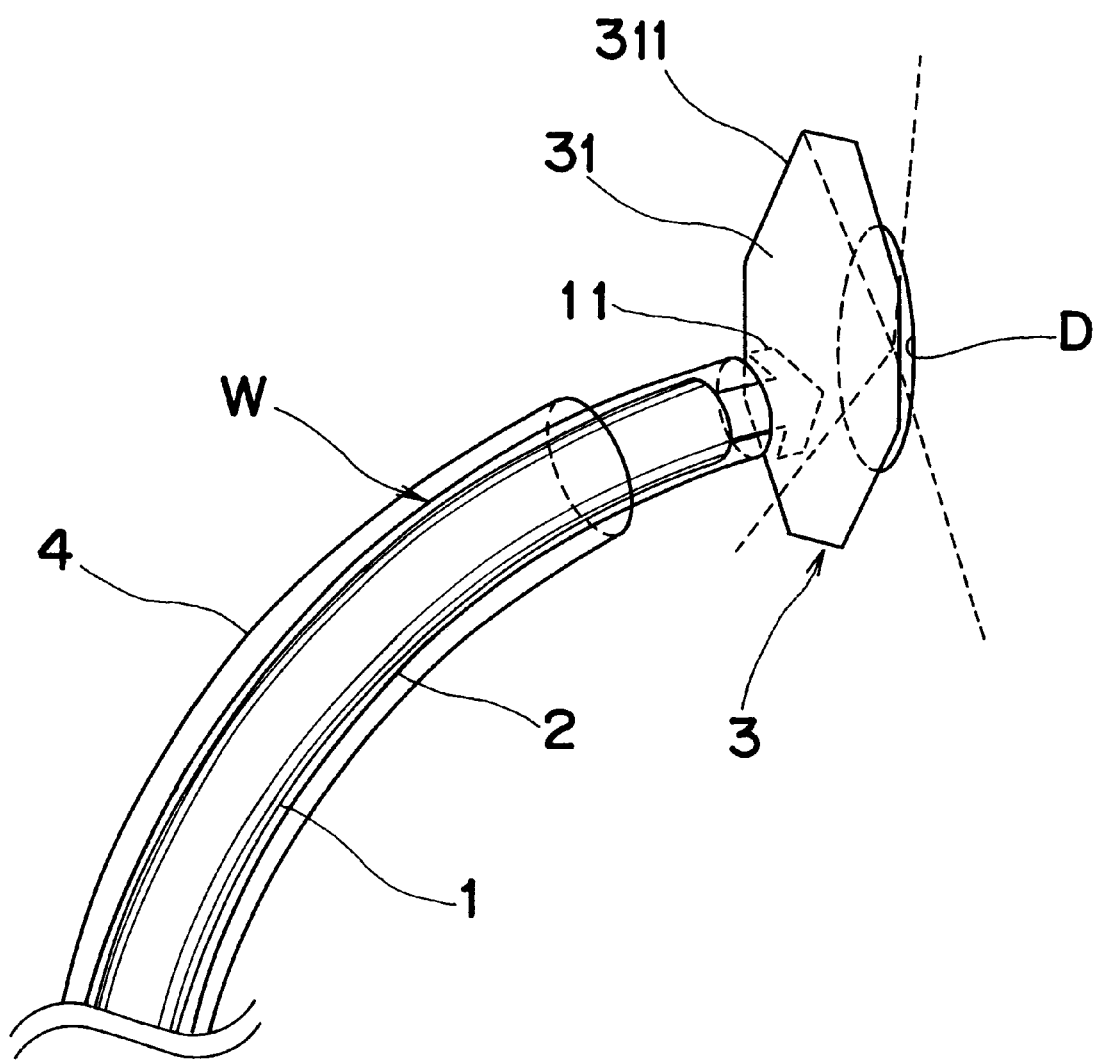
Figure 4:
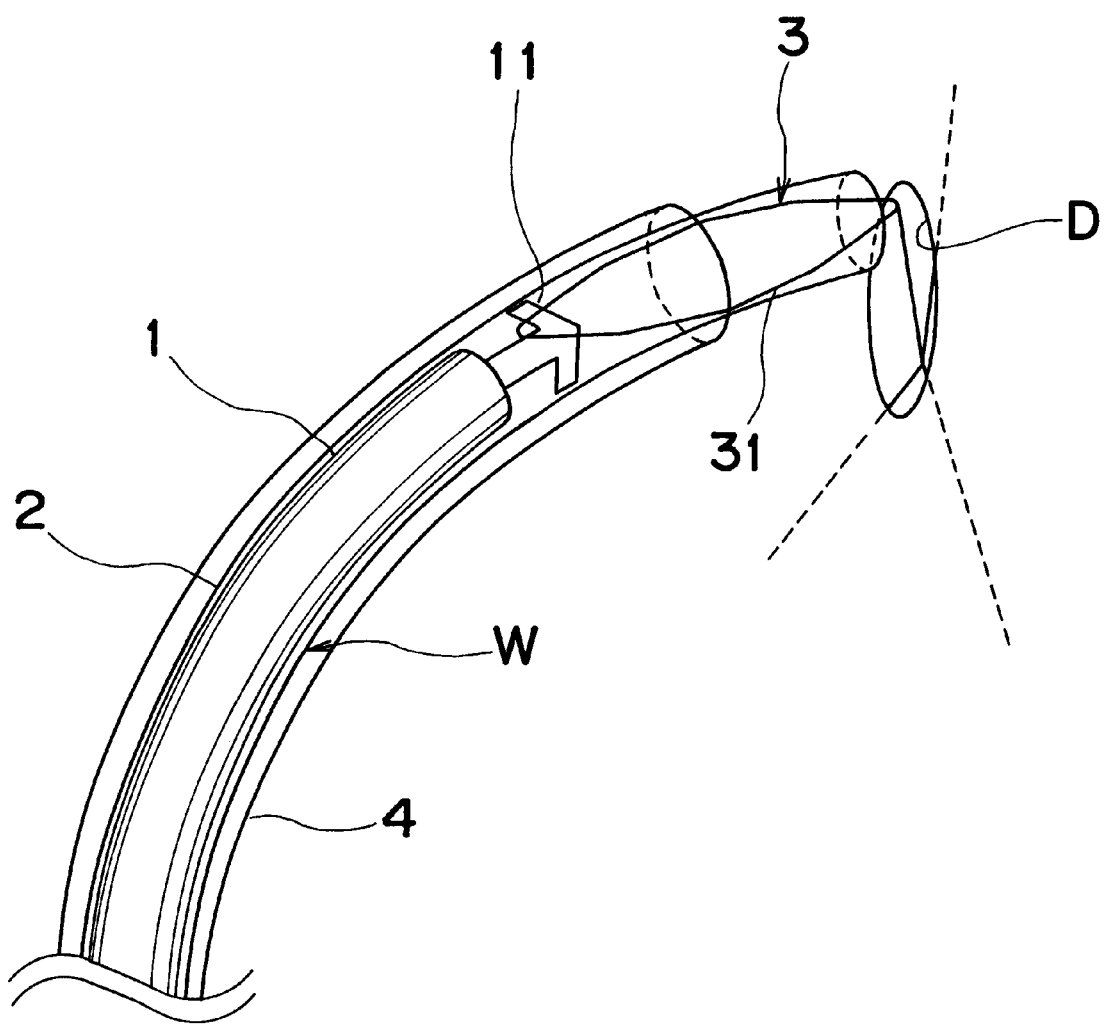
Figure 5:
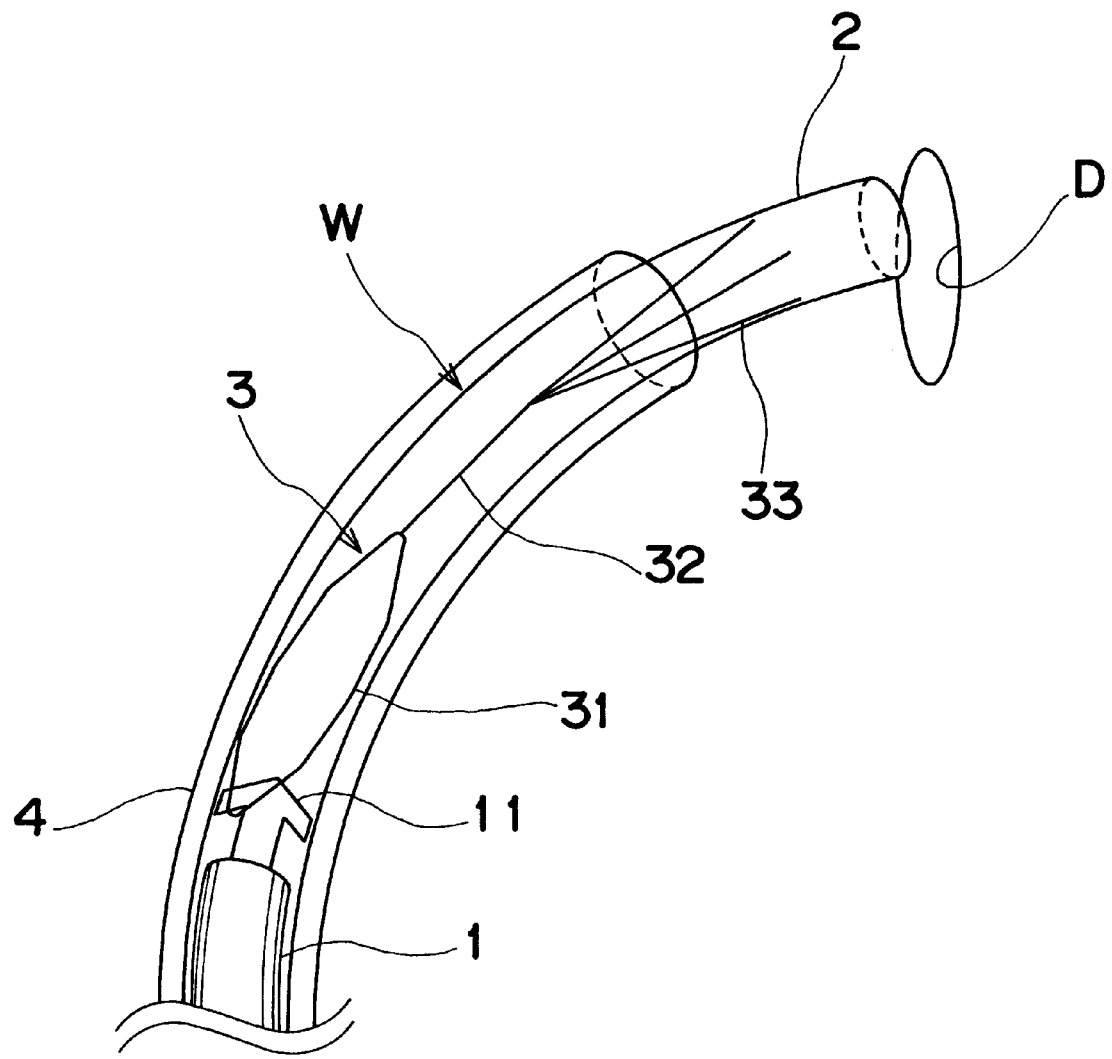
Figure 6:
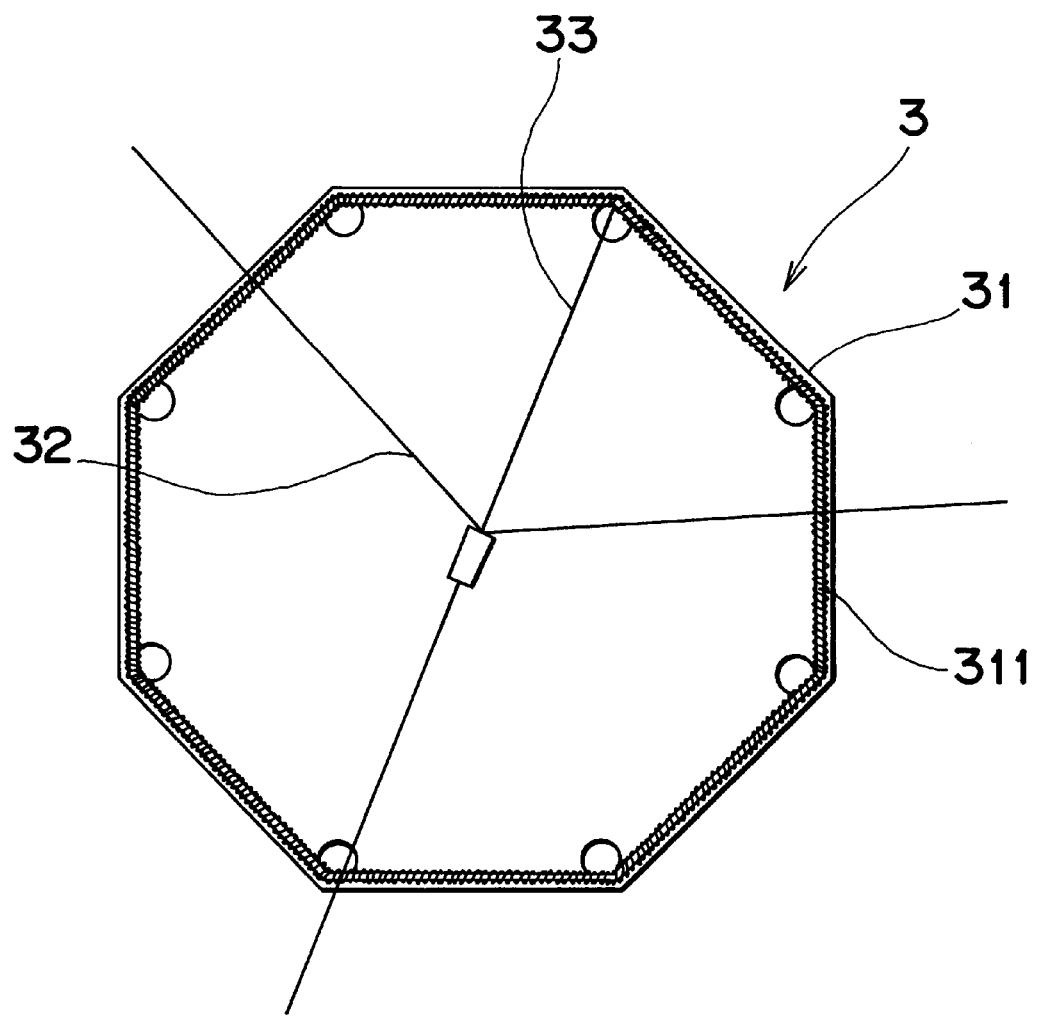
FIG. 6 is a plane view illustrating a defect closure device to be retrieved by a device for retrieval of closure devices according to the present invention.

Firstly, the device W for retrieval of defect closure devices is inserted into an elongated guide sheath 4 which has been previously introduced into the right atrial of a patient through a femoral vein of the right leg of the patient, and then introduced into the right atrial of the patient (FIG. 2). The closure-catching means 11 of the closure-catch catheter 1 is pushed into the guide sheath 4 so that it penetrates the closure member 31 of the closure device 3 at a position close to the frame 311 of the closure device 3. The sheath 2 is then pushed out of the guide sheath 4 until the distal end of the sheath 2 comes into contact with the closure device 3 (FIG. 3). When the catheter 1 is pulled back under such a condition, the closure-catching means 11 catches the frame 311 of the closure member 31 at the arrowhead portion thereof so that the closure device 3 is folded up and pulled in the sheath 2 (FIG. 4). By further pulling back the closure-catch catheter 1, the elastic member 33 is inflected in the longitudinal direction thereof and then the fixing member 32 is folded up and pulled in the sheath 2 (FIG. 5).

As will be understood from the above, it is possible with the device of the present invention to retrieve the defect closure devices from the repaired site in the body of a patient in cases where the defect-closure device has fallen away or dislodged after operation.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A device for retrieval of closure devices comprising:

a closure-catch catheter having closure-catching means at a distal end thereof for catching a closure device, the closure-catch catheter further having a grip at a proximal end thereof, the grip operating the closure-catching means and the closure-catching means having an arrowhead shape; and an elongated sheath having a lumen, the catheter being moveably insertable in the lumen.

2. The device according to claim 1, further comprising a lateral injection tube and a hemostatic device at a proximal end of the sheath.

3. The device according to claim 2, wherein the hemostatic device is one of a packing and O-ring.

4. The device according to claim 1, wherein the grip is a finger grip for manipulating the catheter.

5. The device according to claim 1, wherein the closure-catch catheter comprises an elongated stem portion having a diameter slightly smaller than that of the lumen of the elongated sheath to allow the catheter to be pulled in the sheath smoothly without hooking on the distal end of the sheath.

6. The device according to claim 1, wherein the closure-catch catheter has an arrowhead shape.

* * * * *